United States Patent
Coulson et al.

(10) Patent No.: US 9,623,229 B2
(45) Date of Patent: Apr. 18, 2017

(54) ANTIMICROBIAL STRAW

(71) Applicant: Eldon James Corp., Denver, CO (US)

(72) Inventors: William A. Coulson, Fort Collins, CO (US); Marcia Coulson, Fort Collins, CO (US)

(73) Assignee: WilMarc Holdings, LLC, Fort Collins, CO (US)

(*) Notice: Subject to any disclaimer, the term of this patent is extended or adjusted under 35 U.S.C. 154(b) by 137 days.

(21) Appl. No.: 14/609,319

(22) Filed: Jan. 29, 2015

(65) Prior Publication Data

US 2015/0209567 A1 Jul. 30, 2015

Related U.S. Application Data

(60) Provisional application No. 61/933,228, filed on Jan. 29, 2014.

(51) Int. Cl.

| | |
|---|---|
| *F16L 9/14* | (2006.01) |
| *A61M 39/08* | (2006.01) |
| *A47G 21/18* | (2006.01) |
| *A01N 59/16* | (2006.01) |
| *A01N 25/10* | (2006.01) |
| *A01N 25/34* | (2006.01) |
| *A61L 29/12* | (2006.01) |
| *A61L 29/16* | (2006.01) |
| *A61J 7/00* | (2006.01) |
| *A61J 15/00* | (2006.01) |

(52) U.S. Cl.
CPC ............ *A61M 39/08* (2013.01); *A01N 25/10* (2013.01); *A01N 25/34* (2013.01); *A01N 59/16* (2013.01); *A47G 21/18* (2013.01); *A47G 21/183* (2013.01); *A61L 29/126* (2013.01); *A61L 29/16* (2013.01); *A61J 7/0038* (2013.01); *A61J 15/0026* (2013.01); *A61L 2300/104* (2013.01); *A61L 2300/404* (2013.01); *A61M 2205/0205* (2013.01); *A61M 2207/00* (2013.01)

(58) Field of Classification Search
CPC .. B05D 7/02; B05D 7/222; C09D 5/14; Y10T 428/1393; Y10T 428/1352
USPC ............. 138/145, 146; 428/36.91, 35.7, 35.8
See application file for complete search history.

(56) References Cited

U.S. PATENT DOCUMENTS

| | | | |
|---|---|---|---|
| 4,923,450 A | * | 5/1990 | Maeda .................... A61L 29/16 523/122 |
| 5,048,572 A | | 9/1991 | Levine |
| | | | (Continued) |

OTHER PUBLICATIONS

U.S. Appl. No. 61/933,228, filed Jan. 29, 2014.

*Primary Examiner* — Patrick F Brinson
(74) *Attorney, Agent, or Firm* — Craig R. Miles; CR MILES P.C.

(57) ABSTRACT

A polymeric tubular conduit including a polymeric tubular conduit wall having an outer tubular layer coaxially overlaying an inner tubular layer which defines a continuous tubular passage along a polymeric tubular conduit length of the polymeric tubular conduit; whereby the outer tubular layer, the inner tubular layer, or combinations thereof, include an amount of antimicrobial agent. The amount of antimicrobial agent can be sufficient to kill or inhibit growth of microorganisms in contact with a corresponding polymeric tubular conduit wall external surface, polymeric tubular conduit wall internal surface, or combinations thereof, of the polymeric tubular conduit wall.

19 Claims, 7 Drawing Sheets

(56) References Cited

U.S. PATENT DOCUMENTS

| | | | |
|---|---|---|---|
| 5,332,160 A * | 7/1994 | Ruskin | F16L 11/045 |
| | | | 138/137 |
| 5,894,042 A * | 4/1999 | Ferralli | B05D 7/02 |
| | | | 138/145 |
| 6,736,409 B2 | 5/2004 | Hollenberg | |
| 6,866,498 B2 | 3/2005 | Sagar et al. | |
| 7,083,291 B1 | 8/2006 | Yong et al. | |
| 7,150,411 B2 | 12/2006 | Sheedy | |
| 7,172,559 B2 | 2/2007 | Yong et al. | |
| 7,195,602 B2 | 3/2007 | Yong et al. | |
| 7,381,751 B2 * | 6/2008 | Sarangapani | A61K 31/555 |
| | | | 424/604 |
| 7,584,900 B2 | 9/2009 | White et al. | |
| 7,637,439 B1 | 12/2009 | Highsmith et al. | |
| 7,666,667 B2 | 2/2010 | Yong | |
| 7,767,448 B2 | 8/2010 | Yong | |
| 8,025,242 B2 | 9/2011 | Efremkin et al. | |
| 8,485,453 B2 | 7/2013 | Efremkin et al. | |
| 8,491,855 B2 | 7/2013 | Yong | |
| 8,753,692 B2 * | 6/2014 | Gawande | A01N 59/12 |
| | | | 424/618 |
| 8,852,439 B2 | 10/2014 | Frauchiger et al. | |
| 2008/0197141 A1 * | 8/2008 | Felfoldi | A47G 21/183 |
| | | | 220/705 |
| 2010/0051527 A1 * | 3/2010 | Frandsen | A47G 21/188 |
| | | | 210/209 |
| 2010/0247889 A1 | 9/2010 | Kliesch et al. | |
| 2011/0311647 A1 * | 12/2011 | Gawande | A01N 59/12 |
| | | | 424/618 |
| 2013/0052277 A1 | 2/2013 | Weiss et al. | |
| 2014/0322351 A1 * | 10/2014 | Gawande | A01N 59/12 |
| | | | 424/618 |

* cited by examiner

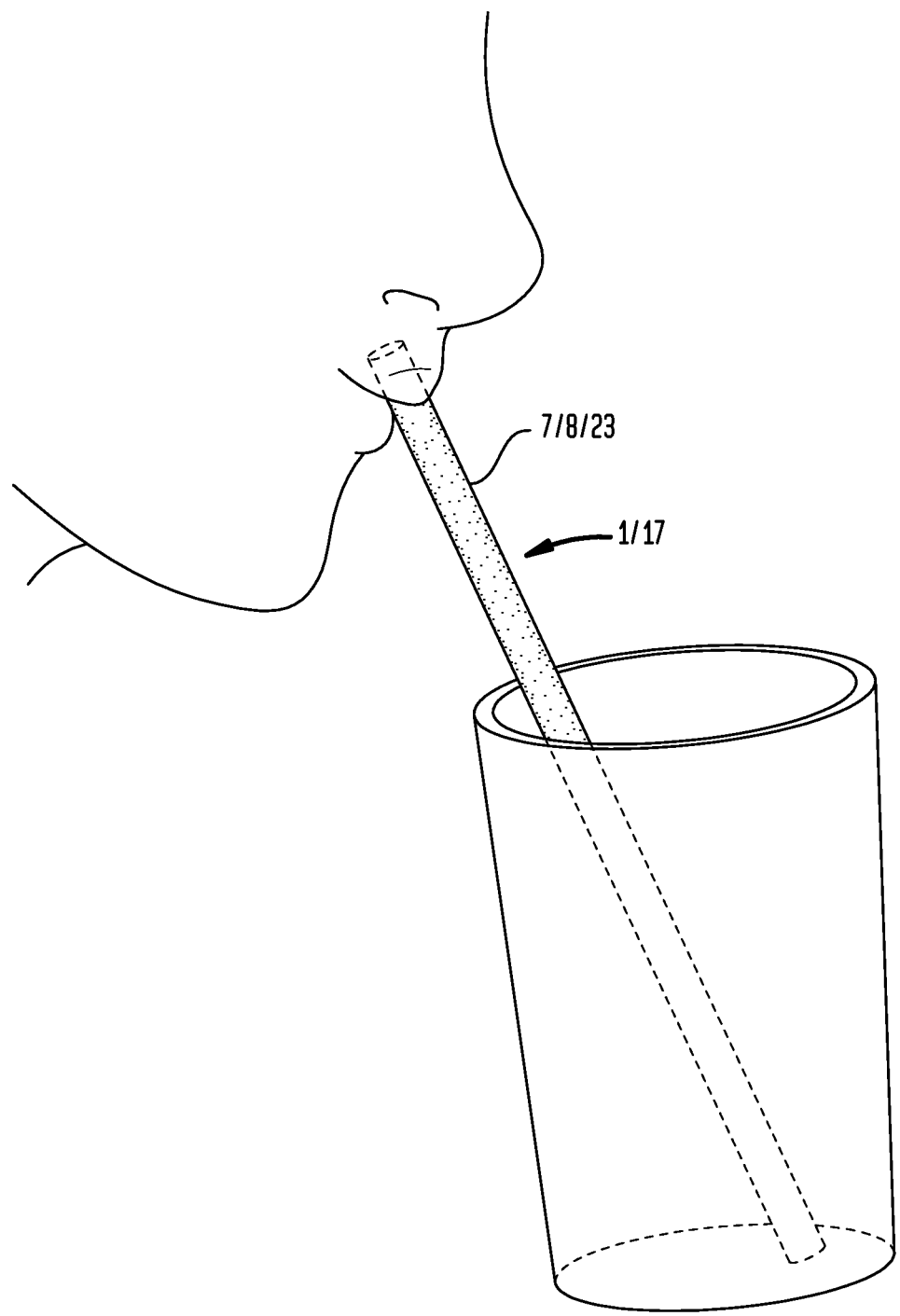

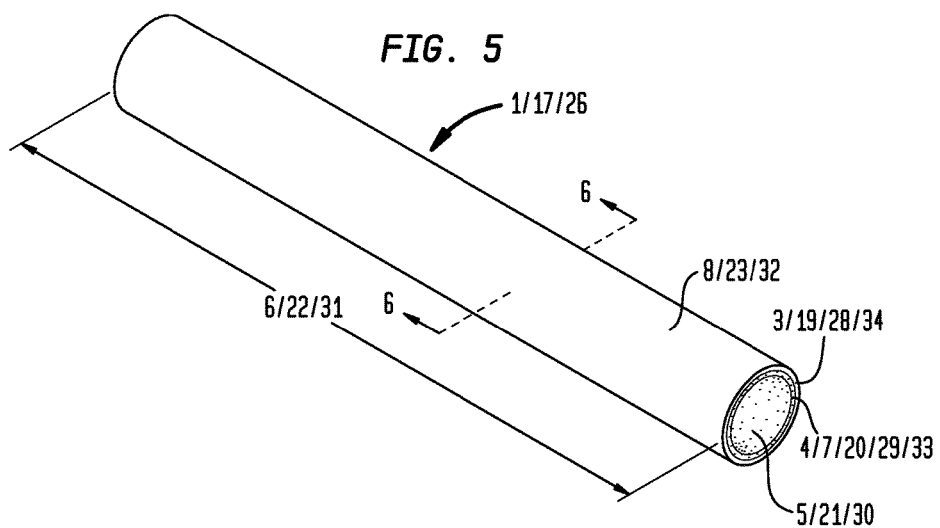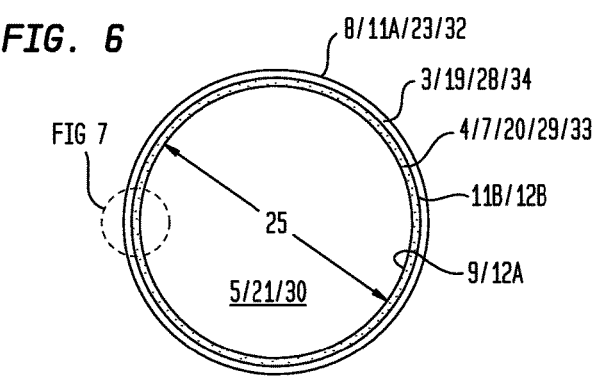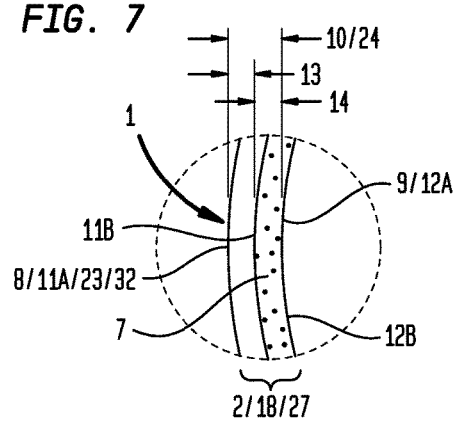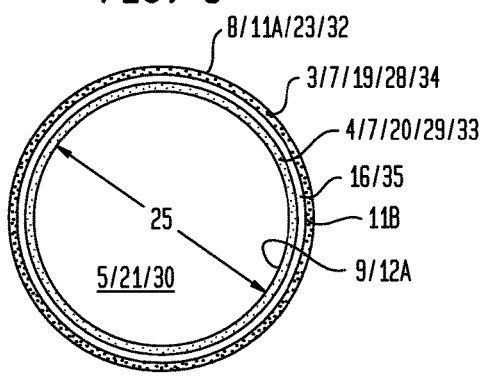

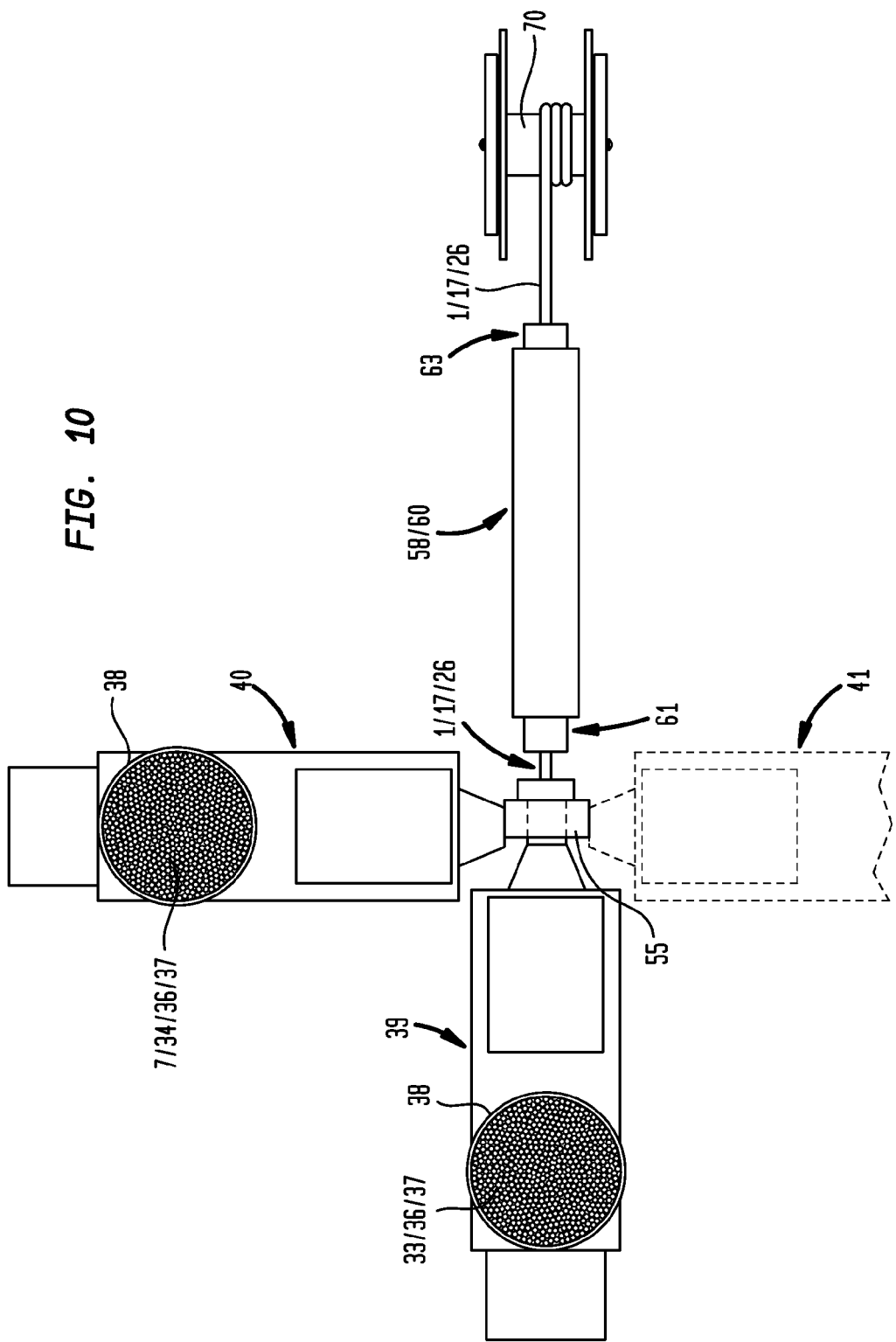

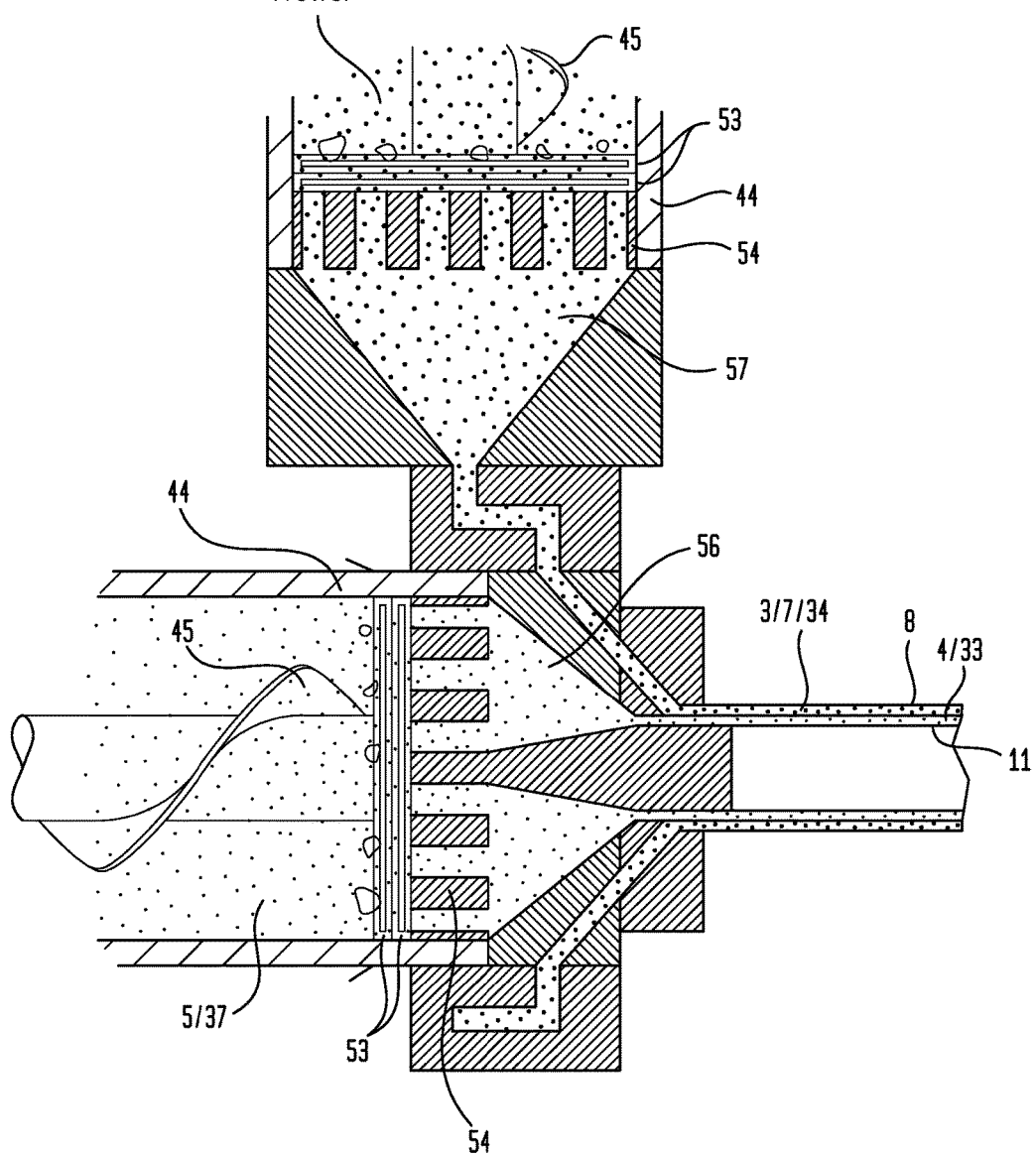

ANTIMICROBIAL STRAW

This U.S. Non-Provisional Patent Application claims the benefit of U.S. Provisional Patent Application No. 61/933,228, filed Jan. 29, 2014, hereby incorporated by reference herein.

I. BACKGROUND OF THE INVENTION

Conventional fluid conveying conduits, whether for conveyance of gases or liquids, are ubiquitous. The use of fluid conveying conduits necessitates handling or contact of the of fluid conveying conduit external surface which can result in deposition or placement of microorganisms or other pathogens on the of fluid conveying conduits external surface, which may then be subsequently transferred to other surfaces or persons.

For example, drinking straws, which are typically open to the environment and repeatedly drawn to the user's mouth, can be inoculated with microorganisms or other pathogens which can infect or reinfect the user and, when disposed of, may be handled by other persons or contact other surfaces, resulting in transfer of the microorganisms or other pathogens to those persons or surfaces.

As an additional example, medical tubing, which may be used to convey oxygen, liquids, or drugs to a person, can also be inoculated with microorganisms or other pathogens. In order for the person to be mobile while using the medical tubing, the length of medical tubing extending between the person and the dispensing station is often long. As a result, lengths of medical tubing may lie along the floor, on bedding, or contact other persons during normal use, thereby becoming a host for microorganisms or other pathogens which may then be transferred to the user using the fluid conveying conduit, other persons, or surfaces.

II. SUMMARY OF THE INVENTION

Accordingly, a broad object of a particular embodiment of the invention can be to provide polymeric tubular conduit including a polymeric tubular conduit wall having an outer tubular layer coaxially overlaying an inner tubular layer which defines a continuous tubular passage along a polymeric tubular conduit length of the polymeric tubular conduit; whereby the outer tubular layer includes an amount of antimicrobial agent. The amount of antimicrobial agent can be sufficient to kill or inhibit growth of microorganisms in contact with a polymeric tubular conduit wall external surface of the polymeric tubular conduit wall.

Another broad object of a particular embodiment of the invention can be to provide polymeric tubular conduit which forms a drinking straw including a drinking straw wall having a drinking straw outer tubular layer coaxially overlaying a drinking straw inner tubular layer which defines a drinking straw continuous tubular passage along a drinking straw length of the drinking straw; whereby the drinking straw outer tubular layer includes an amount of antimicrobial agent. The amount of antimicrobial agent can be sufficient to kill or inhibit growth of microorganisms in contact with a drinking straw wall external surface of the drinking straw wall.

Another broad object of a particular embodiment of the invention can be to provide polymeric tubular conduit which forms medical tubing including a medical tubing wall having a medical tubing outer tubular layer coaxially overlaying a medical tubing inner tubular layer which defines a medical tubing continuous tubular passage along a medical tubing length of the medical tubing; whereby the medical tubing outer tubular layer includes an amount of antimicrobial agent. The amount of antimicrobial agent can be sufficient to kill or inhibit growth of microorganisms in contact with a medical tubing wall external surface of the medical tubing wall.

Another broad object of a particular embodiment of the invention can be to provide a method of making a polymeric tubular conduit, the method including providing a polymeric tubular conduit wall having an outer tubular layer coaxially overlaying an inner tubular layer which defines a continuous tubular passage along a polymeric tubular conduit length of the polymeric tubular conduit; whereby the outer tubular layer comprises an amount of antimicrobial agent. The amount of antimicrobial agent can be sufficient to kill or inhibit growth of microorganisms in contact with the polymeric tubular conduit wall external surface of the polymeric tubular conduit wall.

Another broad object of a particular embodiment of the invention can be to provide polymeric tubular conduit including a polymeric tubular conduit wall having an outer tubular layer coaxially overlaying an inner tubular layer which defines a continuous tubular passage along a polymeric tubular conduit length of the polymeric tubular conduit; whereby the inner tubular layer includes an amount of antimicrobial agent. The amount of antimicrobial agent can be sufficient to kill or inhibit growth of microorganisms in contact with a polymeric tubular conduit wall internal surface of the polymeric tubular conduit wall.

Another broad object of a particular embodiment of the invention can be to provide a method of making a polymeric tubular conduit, the method including providing a polymeric tubular conduit wall having an outer tubular layer coaxially overlaying an inner tubular layer which defines a continuous tubular passage along a polymeric tubular conduit length of the polymeric tubular conduit; whereby the inner tubular layer comprises an amount of antimicrobial agent. The amount of antimicrobial agent can be sufficient to kill or inhibit growth of microorganisms in contact with the polymeric tubular conduit wall internal surface of the polymeric tubular conduit wall.

Naturally, further objects of the invention are disclosed throughout other areas of the specification, drawings, and claims.

III. BRIEF DESCRIPTION OF THE DRAWINGS

FIG. 1A is an illustration of a particular embodiment of a polymeric tubular conduit which forms a drinking straw.

Figure 2:
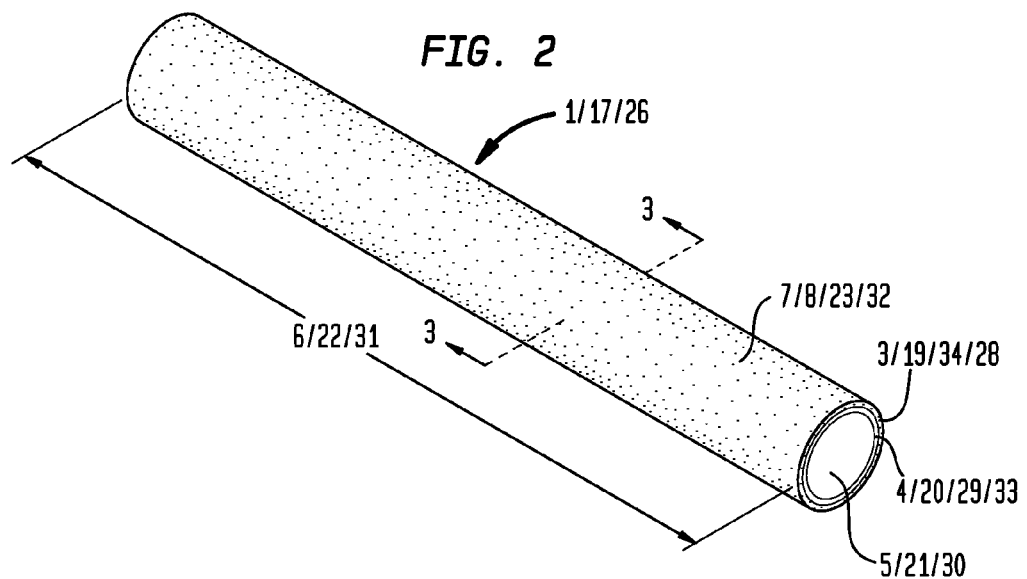

FIG. 2 is a perspective view of a particular embodiment of a polymeric tubular conduit having an inner tubular layer formed from a first polymeric material and an outer tubular layer formed from a second polymeric material, the outer tubular layer having an amount of antimicrobial agent sufficient to kill or inhibit growth of microorganisms in contact with a polymeric tubular conduit wall external surface of the polymeric tubular conduit wall.

Figure 3:
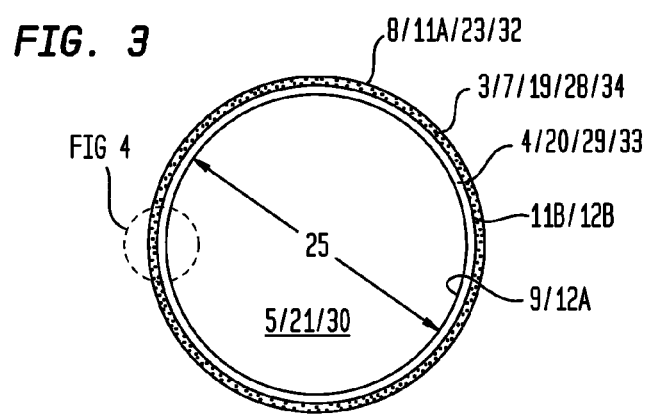

FIG. 3 is a cross-section 3-3 of the particular embodiment of a polymeric tubular conduit shown in FIG. 2.

Figure 4:
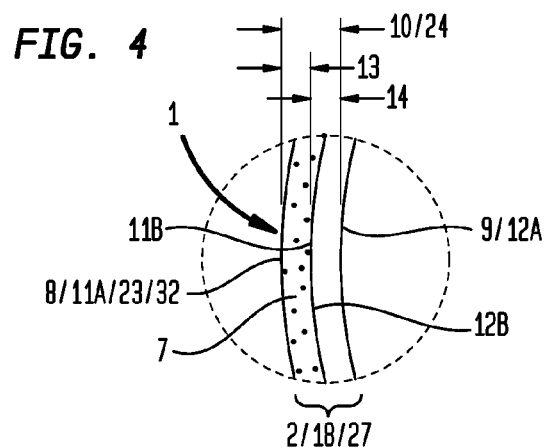

FIG. 4 is an enlarged view of a portion of the particular embodiment of a polymeric tubular conduit shown in FIG. 3.

FIG. 5 is a perspective view of a particular embodiment of a polymeric tubular conduit having an inner tubular layer formed from a first polymeric material and an outer tubular layer formed from a second polymeric material, the inner tubular layer having an amount of antimicrobial agent sufficient to kill or inhibit growth of microorganisms in contact with a polymeric tubular conduit wall internal surface of the polymeric tubular conduit wall.

FIG. 6 is a cross-section 6-6 of the particular embodiment of a polymeric tubular conduit shown in FIG. 5.

FIG. 7 is an enlarged view of a portion of the particular embodiment of a polymeric tubular conduit shown in FIG. 6.

FIG. 8 is a cross-sectional view of a particular embodiment of a polymeric tubular conduit having an inner tubular layer formed from a first polymeric material, an outer tubular layer formed from a second polymeric material, and one or more intermediate layers formed from additional polymeric materials, the outer and inner tubular layers having an amount of antimicrobial agent sufficient to kill or inhibit growth of microorganisms in contact with corresponding polymeric tubular conduit wall external and internal surfaces of the polymeric tubular conduit wall.

Figure 9:
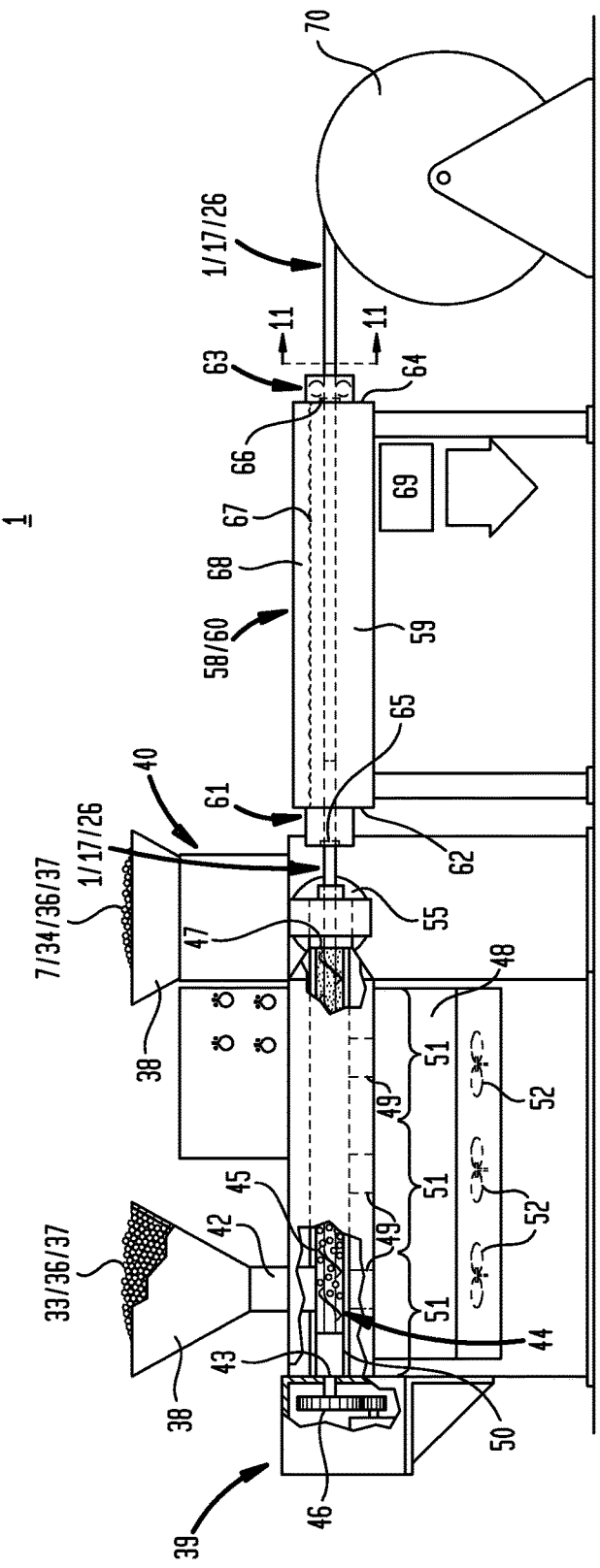

FIG. 9 is side view of a co-extrusion system adapted for production of particular embodiments of a polymeric tubular conduit.

FIG. 10 is top view of a co-extrusion system adapted for production of particular embodiments of a polymeric tubular conduit.

FIG. 11 is cross-section 11-11 of the die shown in FIG. 9 through which molten first polymeric material and molten second polymeric material passes in the production of a particular embodiment of a polymeric tubular conduit having an inner tubular layer formed from the molten first polymeric material and an outer tubular layer formed from the molten second polymeric material.

IV. DETAILED DESCRIPTION OF THE INVENTION

Now referring primarily to FIG. 1A through FIG. 4, which illustrate particular embodiments of a polymeric tubular conduit (1) including a polymeric tubular conduit wall (2) having an outer tubular layer (3) coaxially overlaying an inner tubular layer (4) which defines a continuous tubular passage (5) along a polymeric tubular conduit length (6) of the polymeric tubular conduit (1), whereby the outer tubular layer (3) includes an amount of antimicrobial agent (7). The amount of antimicrobial agent (7) can be sufficient to kill or inhibit growth of microorganisms in contact with a polymeric tubular conduit wall external surface (8) of the polymeric tubular conduit wall (2).

Now referring primarily to FIG. 5 through FIG. 7, which illustrate another particular embodiment of a polymeric tubular conduit (1) including a polymeric tubular conduit wall (2) having an outer tubular layer (3) coaxially overlaying an inner tubular layer (4) which defines a continuous tubular passage (5) along a polymeric tubular conduit length (6) of the polymeric tubular conduit (1), whereby the inner tubular layer (4) includes an amount of antimicrobial agent (7). The amount of antimicrobial agent (7) can be sufficient to kill or inhibit growth of microorganisms in contact with a polymeric tubular conduit wall internal surface (9) of the polymeric tubular conduit wall (2).

The term "polymeric tubular conduit" for the purposes of the present invention means a tubular conduit formed from one or more polymeric materials. Typically, but not necessarily, the tubular conduit can have a generally circular cross-section.

The term "polymeric material" for the purposes of the present invention means one or more thermoplastic polymers which can be heated and reformed, and without limitation to the breadth of the forgoing, can include as illustrative examples: thermoplastic elastomers such as styrene block copolymers, polyolefin blends, elastomeric alloys, thermoplastic polyurethanes, thermoplastic copolyesters, thermoplastic polyamides, polypropylene, polyethylene, high density polyethylene, low density polyethylene, polyethylene terephthalate, poly-1,4-cyclohexanedimethylene terephthalate, polyethylene 2,6-naphthalate bibenzoate, polyolefin, polyvinylidene fluoride, polyethylene 2,6-naphthalate, acrylonitrile butadiene styrene, polyvinylchloride, polyether block amide, or the like, or combinations thereof.

The term "antimicrobial agent" for the purposes of the present invention means an agent which can be combined with a polymeric material in sufficient amounts to kill or inhibit growth of microorganisms in contact with the polymeric material.

The terms "combining, combined, or combination" for the purposes of the present invention mean putting two or more materials together. Such methods can include, but are not limited to, mixing, blending, commingling, concocting, homogenizing, incorporating, intermingling, fusing, joining, shuffling, stirring, coalescing, integrating, confounding, uniting, or the like, or combinations thereof.

The term "microorganism" for the purposes of the present invention means any organism of microscopic or submicroscopic size, whether a virus, a single cell organism, or a multicellular organism. Without limitation to the breadth of the foregoing, microorganisms can include viruses; prokaryotes, such as bacteria and archaea; eukaryotes, such as protists, fungi, plants, and animals; or combinations thereof.

Now referring primarily to FIG. 4 and FIG. 7, the polymeric tubular conduit wall (2) can include a polymeric tubular conduit wall thickness (10) disposed between the polymeric tubular conduit wall external surface (8) defined by an outer tubular layer external surface (11A) of the outer tubular layer (3) and the polymeric tubular conduit wall internal surface (9) defined by an inner tubular layer internal surface (12A) of the inner tubular layer (4). As to particular embodiments, the polymeric tubular conduit wall thickness (10) can have a range of between about 0.05 millimeters to about 0.25 millimeters.

As to particular embodiments, the polymeric tubular conduit wall thickness (10) can be selected from the group including or consisting of: between about 0.05 millimeters to about 0.1 millimeters; between about 0.075 millimeters to about 0.125 millimeters; between about 0.1 millimeters to about 0.15 millimeters; between about 0.125 millimeters to about 0.175 millimeters; between about 0.15 millimeters to about 0.2 millimeters; between about 0.175 millimeters to about 0.225 millimeters; and between about 0.2 millimeters to about 0.25 millimeters.

As to particular embodiments, the polymeric tubular conduit wall thickness (10) can be generally uniform along the polymeric tubular conduit length (6) whereas, as to other particular embodiments, the polymeric tubular conduit wall thickness (10) can be non-uniform along the polymeric tubular conduit length (6), depending upon the application.

Again referring primarily to FIG. 4 and FIG. 7, the outer tubular layer (3) can include an outer tubular layer thickness (13) disposed between the outer tubular layer external surface (11A) and an outer tubular layer internal surface (11B). In addition, the inner tubular layer (4) can include an inner tubular layer thickness (14) disposed between an inner tubular layer external surface (12B) and the inner tubular layer internal surface (11). As to particular embodiments, the outer and inner tubular layer thicknesses (13)(14) can be generally similar along the polymeric tubular conduit length (6) whereas, as to other particular embodiments, the outer and inner tubular layers thicknesses (13)(14) can be dissimilar along the polymeric tubular conduit length (6).

As an illustrative example of a particular embodiment of a polymeric tubular conduit wall (2) having dissimilar outer and inner tubular layers thicknesses (13)(14), the outer tubular layer (3) can be formed from polyethylene terephthalate, which can impart a relatively rigid and smooth polymeric tubular conduit wall external surface (8) to the polymeric tubular conduit wall (2) and the inner tubular layer (4) can be formed from polypropylene, polyolefin, or a polyolefin blend, which can impart flexibility to the polymeric tubular conduit wall (2). As to this particular embodiment, the outer tubular layer thickness (13) can be in a range of between about 10% to about 25% of the polymeric tubular conduit wall thickness (10). For example, a polymeric tubular conduit wall (2) having a polymeric tubular conduit wall thickness (10) in a range of between about 0.05 millimeters to about 0.1 millimeters can include an outer tubular layer (3) having an outer tubular layer thickness (13) in a range of between about 0.005 millimeters to about 0.025 millimeters.

As to particular embodiments of a polymeric tubular conduit (1) whereby the outer tubular layer (3) imparts rigidity to the polymeric tubular conduit wall external surface (8) and the inner tubular layer (4) imparts flexibility to the polymeric tubular conduit wall (2), the outer tubular layer thickness (13) can be adjusted to impart a desired amount of flexibility to the polymeric tubular conduit wall (2). For example, a lesser outer tubular layer thickness (13) can impart greater flexibility to the polymeric tubular conduit wall (2) in relation to a greater outer tubular layer thickness (13), which can impart lesser flexibility to the polymeric tubular conduit wall (2).

As to particular embodiments of a polymeric tubular conduit (1) whereby the outer tubular layer (3) includes an amount of antimicrobial agent (7), a lesser outer tubular layer thickness (13) can require a lesser amount of antimicrobial agent (7) in relation to an outer tubular layer (3) having a greater outer tubular layer thickness (13), which may lower the cost of production. As to particular embodiments, such as one-time use or disposable polymeric tubular conduits (1), a lesser cost of production may be desirable.

As to particular embodiments of the polymeric tubular conduit wall (2), only the outer tubular layer (3) can include an amount of antimicrobial agent (7). As to other particular embodiments of the polymeric tubular conduit wall (2), only the inner tubular layer (4) can include an amount of antimicrobial agent (7). As to yet other particular embodiments of the polymeric tubular conduit wall (2), both the outer and inner tubular layers (3)(4) can include corresponding amounts of antimicrobial agent (7).

Now referring primarily to FIG. 8, as to particular embodiments, the polymeric tubular conduit wall (2) can further include one or more intermediate layers (16) disposed between the inner and outer tubular layers (4)(3), whereby the one or more intermediate layers (16) can include an amount of antimicrobial agent (7) or be void of an amount of antimicrobial agent (7), depending upon the application.

As to particular embodiments, the outer, inner, or intermediate tubular layer (3)(4)(16) can include an amount of antimicrobial agent (7) in a range of between about 0.01% to about 15% by weight of the corresponding outer, inner, or intermediate tubular layer (3)(4)(16), depending upon the antimicrobial agent (7), the application, or combinations thereof.

As to particular embodiments, the amount of antimicrobial agent (7) can be selected from the group including or consisting of: between about 0.01% to about 1% by weight of the corresponding outer, inner, or intermediate tubular layer (3)(4)(16); between about 0.5% to about 1.5% by weight of the corresponding outer, inner, or intermediate tubular layer (3)(4)(16); between about 1% to about 2% by weight of the corresponding outer, inner, or intermediate tubular layer (3)(4)(16); between about 1.5% to about 2.5% by weight of the corresponding outer, inner, or intermediate tubular layer (3)(4)(16); between about 2% to about 3% by weight of the corresponding outer, inner, or intermediate tubular layer (3)(4)(16); between about 2.5% to about 3.5% by weight of the corresponding outer, inner, or intermediate tubular layer (3)(4)(16); between about 3% to about 4% by weight of the corresponding outer, inner, or intermediate tubular layer (3)(4)(16); between about 3.5% to about 4.5% by weight of the corresponding outer, inner, or intermediate tubular layer (3)(4)(16); between about 4% to about 5% by weight of the corresponding outer, inner, or intermediate tubular layer (3)(4)(16); between about 4.5% to about 5.5% by weight of the corresponding outer, inner, or intermediate tubular layer (3)(4)(16); between about 5% to about 6% by weight of the corresponding outer, inner, or intermediate tubular layer (3)(4)(16); between about 5.5% to about 6.5% by weight of the corresponding outer, inner, or intermediate tubular layer (3)(4)(16); between about 6% to about 7% by weight of the corresponding outer, inner, or intermediate tubular layer (3)(4)(16); between about 6.5% to about 7.5% by weight of the corresponding outer, inner, or intermediate tubular layer (3)(4)(16); between about 7% to about 8% by weight of the corresponding outer, inner, or intermediate tubular layer (3)(4)(16); between about 7.5% to about 8.5% by weight of the corresponding outer, inner, or intermediate tubular layer (3)(4)(16); between about 8% to about 9% by weight of the corresponding outer, inner, or intermediate tubular layer (3)(4)(16); between about 8.5% to about 9.5% by weight of the corresponding outer, inner, or intermediate tubular layer (3)(4)(16); between about 9% to about 10% by weight of the corresponding outer, inner, or intermediate tubular layer (3)(4)(16); between about 9.5% to about 10.5% by weight of the corresponding outer, inner, or intermediate tubular layer (3)(4)(16); between about 10% to about 11% by weight of the corresponding outer, inner, or intermediate tubular layer (3)(4)(16); between about 10.5% to about 11.5% by weight of the corresponding outer, inner, or intermediate tubular layer (3)(4)(16); between about 11% to about 12% by weight of the corresponding outer, inner, or intermediate tubular layer (3)(4)(16); between about 11.5% to about 12.5% by weight of the corresponding outer, inner, or intermediate tubular layer (3)(4)(16); between about 12% to about 13% by weight of the corresponding outer, inner, or intermediate tubular layer (3)(4)(16); between about 12.5% to about 13.5% by weight of the corresponding outer, inner, or intermediate tubular layer (3)(4)(16); between about 13% to about 14% by weight of the corresponding outer, inner, or intermediate tubular layer (3)(4)(16); between about 13.5% to about 14.5% by weight of the corresponding outer, inner, or intermediate tubular layer (3)(4)(16); and between about 14% to about 15% by weight of the corresponding outer, inner, or intermediate tubular layer (3)(4)(16).

As to particular embodiments, the antimicrobial agent (7) can have a median particle size distribution (D50) in a range of between about 0.5 micrometers to about 15 micrometers.

As to other particular embodiments, the antimicrobial agent (7) can have a median particle size distribution (D50) in a range of between about 3 micrometers to about 10 micrometers.

As to particular embodiments, an antimicrobial agent (7) having a lesser median particle size distribution (D50), for example a median particle size distribution (D50) of less than 1.8 micrometers, can have substantially greater antimicrobial activity at a similar loading in relation to an antimicrobial agent (7) having a greater median particle size distribution (D50), which may result from uniformity of distribution within the corresponding outer, inner, or intermediate tubular layer (3)(4)(16) or from an increased rate of release of the antimicrobial agent (7) within the corresponding outer, inner, or intermediate tubular layer (3)(4)(16).

As to particular embodiments, the antimicrobial agent (7) can include an amount of elemental silver or silver ions (collectively "silver"). As an illustrative example, elemental silver can take the form of nanoparticles, which may be obtained from Bio-Gate AG, Neumeyerstraβe 28-34, 90411 Nürnberg, Germany. As an illustrative example, silver ions can take the form of silver-containing zirconium phosphates, which may be obtained from Milliken & Company, PO Box 1926, Spartanburg, S.C. 29303, United States, or can take the form of silver-containing glasses, which may be obtained from Ciba Specialty Chemicals, Klybeckstrasse 141, CH-4002 Basel, Switzerland, or can take the form of silver-containing zeolites (microporous carriers), which may be obtained from Sciessent, 60 Audubon Road, Wakefield, Mass. 01880, United States.

As to particular embodiments whereby the antimicrobial agent (7) includes silver-containing zeolites, the amount of silver ions in the zeolites can be in a range of between about 0.5% to about 20% by weight of the zeolites.

As to other embodiments whereby the antimicrobial agent (7) includes silver-containing zeolites, the amount of silver ions in the zeolites (such as Product Nos. AJ 10D or LJ 10D, both of which may be obtained from Sciessent, 60 Audubon Road, Wakefield, Mass. 01880, United States) can be around 2.5% by weight of the zeolites.

As to particular embodiments, the outer, inner, or intermediate tubular layer (3)(4)(16) can include an amount of silver sufficient to kill or inhibit growth of microorganisms. As to particular embodiments, the amount of silver can be in a range of between about 0.01% to about 2% by weight of the corresponding outer, inner, or intermediate tubular layer (3)(4)(16).

As an illustrative example, a polymeric tubular conduit (1) can include an outer tubular layer (3) formed from polyethylene terephthalate having an amount of silver in a range of between about 0.5% to about 2% by weight of the outer tubular layer (3).

As to particular embodiments, the antimicrobial agent (7) can include a combination of elements or elemental ions. As an illustrative example, the elements or elemental ions can include silver and zinc. As to particular embodiments, the combination of silver and zinc can include generally similar amounts of silver and zinc.

As to other particular embodiments, the combination of silver and zinc can include a greater amount of silver and a lesser amount of zinc. As to yet other particular embodiments, the combination of zinc and silver can include a lesser amount of silver and a greater amount of zinc.

As to particular embodiments, the combination of silver and zinc can have a ratio in a range of between about 1:1 to about 3:1. As an illustrative example, a polymeric tubular conduit (1) can include an outer tubular layer (3) formed from polyethylene terephthalate having a combination of silver and zinc in a ratio of about 2:1, whereby the combination of silver and zinc can be in a range of between about 0.5% to about 2% by weight of the outer tubular layer (3).

As to other particular embodiments, the combination of silver and zinc can have a ratio of between about 1:1 to about 1:3. As an illustrative example, a polymeric tubular conduit (1) can include an outer tubular layer (3) formed from polyethylene terephthalate having a combination of silver and zinc in a ratio of about 1:2, whereby the combination of silver and zinc can be in a range of between about 0.5% to about 2% by weight of the outer tubular layer (3).

Now referring primarily to FIG. 1A, as to particular embodiments, the polymeric tubular conduit (1) can form a drinking straw (17), for example a drinking straw (17) including a drinking straw wall (18) having a drinking straw outer tubular layer (19) coaxially overlaying a drinking straw inner tubular layer (20) which defines a drinking straw continuous tubular passage (21) along a drinking straw length (22) of the drinking straw (17) through which fluids can be drawn; whereby the drinking straw outer tubular layer (19) includes an amount of antimicrobial agent (7). The amount of antimicrobial agent (7) can be sufficient to kill or inhibit growth of microorganisms which contact a drinking straw wall external surface (23) of the drinking straw wall (18).

The polymeric tubular conduit (1) can be compatible with drinking straws (17) of all common dimensions. Typically, but not necessarily, a drinking straw (17) can have a drinking straw wall thickness (24) in a range of between about 0.4 millimeters to about 0.8 millimeters, with a drinking straw interior diameter (25) in a range of between about 1.6 millimeters to about 9.5 millimeters; however, embodiments of the polymeric tubular conduit (1) for use as a drinking straw (17) can have a lesser or greater drinking straw wall thickness (24) or drinking straw interior diameter (25), depending upon the application.

Typically, but not necessarily, embodiments of the polymeric tubular conduit (1) for use as a drinking straw (17) can have a drinking straw length (22) in a range of between about 75 millimeters to about 300 millimeters; however, embodiments of the polymeric tubular conduit (1) for use as a drinking straw (17) can have a lesser or greater drinking straw length (22), depending upon the application. As an illustrative example, embodiments of the polymeric tubular conduit (1) for use as a drinking straw (17) can have a drinking straw length (22) in a range of between about 190 millimeters to about 197 millimeters.

Figure 1B:
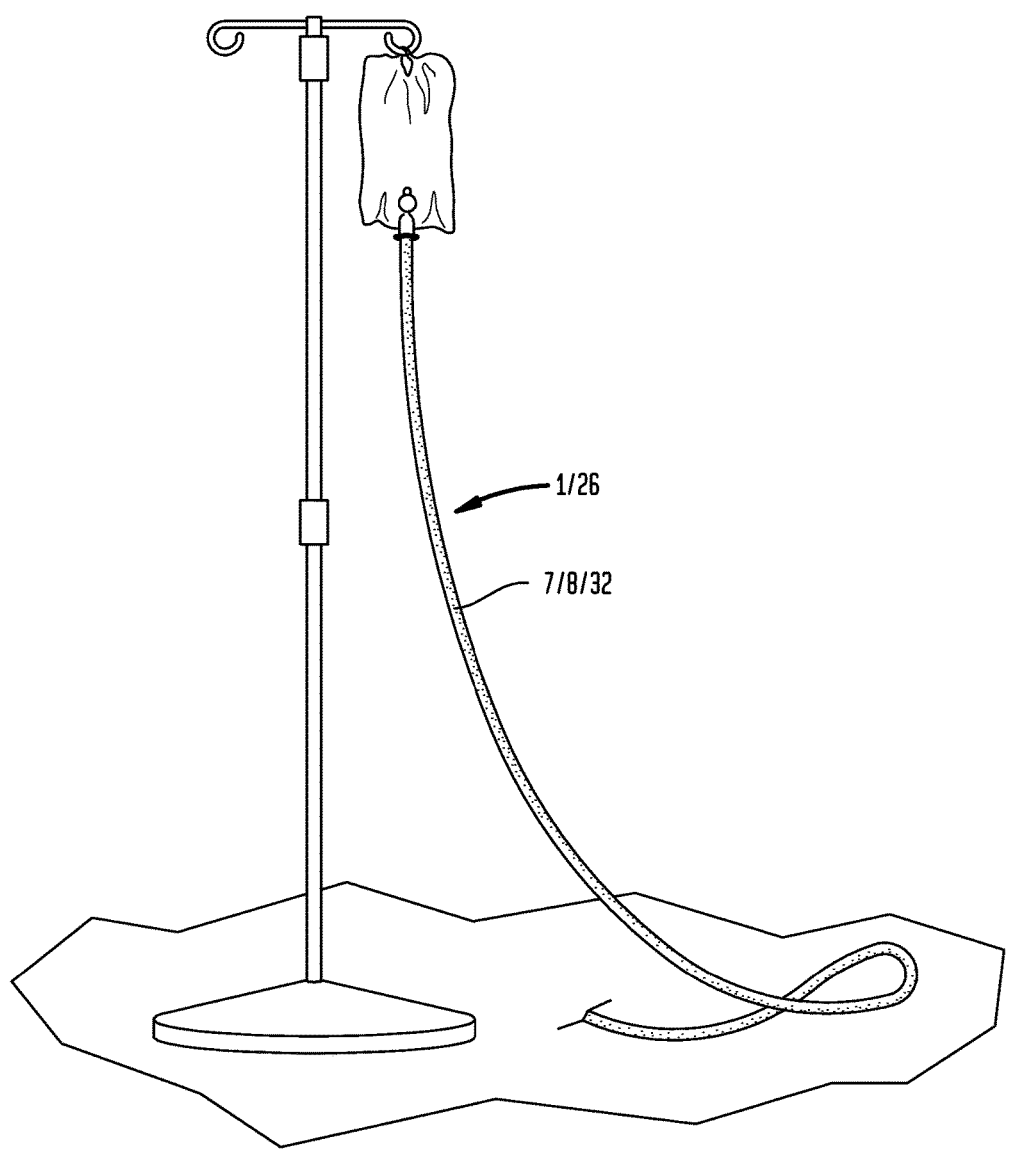
FIG. 1B is an illustration of a particular embodiment of a polymeric tubular conduit which forms medical tubing.

Now referring primarily to FIG. 1B, as to other particular embodiments, the polymeric tubular conduit (1) can form medical tubing (26), for example medical tubing (26) including a medical tubing wall (27) having a medical tubing outer tubular layer (28) coaxially overlaying a medical tubing inner tubular layer (29) which defines a medical tubing continuous tubular passage (30) along a medical tubing length (31) of the medical tubing (26) through which fluids can be drawn; whereby the medical tubing outer tubular layer (28) includes an amount of antimicrobial agent (7). The amount of antimicrobial agent (7) can be sufficient to kill or inhibit growth of microorganisms which contact a medical tubing wall external surface (32) of the medical tubing wall (27).

EXAMPLES

Direct Inoculation Assay

Efficacy of first, second, and third polymeric tubular conduits (1), each having an inner tubular layer (4) including an amount of antimicrobial agent (7), was tested again *Escherichia coli* by a direct inoculation assay, whereby each polymeric tubular conduit internal surface (9) was inoculated with $3.0 \times 10^5$ CFU/mL of *Escherichia coli* and incubated for 24 hours in a sealed container with humidity. Following the incubation, each polymeric tubular conduit (1) was enumerated, whereby the first, second, and third polymeric tubular conduits (1) had corresponding 99.9999%, 99.999%, and 99.999% percent reductions in CFU/mL of *Escherichia coli*. For comparison, the positive control, which was void of an amount of antimicrobial agent (7), had a 6233% percent increase in CFU/mL of *Escherichia coli* following the 24 hour incubation.

Zone of Inhibition Test

As an additional example, efficacy of the polymeric tubular conduit (1) having an outer, inner, or intermediate tubular layer (3)(4)(16) including an amount of antimicrobial agent (7) can be tested against *Escherichia coli* (Gram-negative bacteria), *Staphylococcus aureus* (Gram-positive bacteria), *Aspergillus niger* (fungi), *Cladosporium cladosporioides* (fungi), or *Trichoderma* sp. (fungi) by a zone of inhibition test, as follows.

Test Samples

Control: a polymeric tubular conduit (1) including an outer tubular layer (3) of polyethylene terephthalate having an outer tubular layer thickness (13) thickness of about 0.127 millimeters which does not include an amount of antimicrobial agent (7) and an inner tubular layer (4) of polyolefin having an inner tubular layer thickness (14) of about 0.381 millimeters which does not include an amount of antimicrobial agent (7).

Test Sample 1: a polymeric tubular conduit (1) including an outer tubular layer (3) of polyethylene terephthalate having an outer tubular layer thickness (13) thickness of about 0.127 millimeters which includes an amount of antimicrobial agent (7) comprising silver in an amount of about 0.5% by weight of the outer tubular later (3) and an inner tubular layer (4) of polyolefin having an inner tubular layer thickness (14) of about 0.381 millimeters which does not include an amount of antimicrobial agent (7).

Test Sample 2: a polymeric tubular conduit (1) including an outer tubular layer (3) of polyethylene terephthalate having an outer tubular layer thickness (13) thickness of about 0.127 millimeters which includes an amount of antimicrobial agent (7) comprising silver in an amount of about 1% by weight of the outer tubular later (3) and an inner tubular layer (4) of polyolefin having an inner tubular layer thickness (14) of about 0.381 millimeters which does not include an amount of antimicrobial agent (7).

Test Sample 3: a polymeric tubular conduit (1) including an outer tubular layer (3) of polyethylene terephthalate having an outer tubular layer thickness (13) thickness of about 0.127 millimeters which includes an amount of antimicrobial agent (7) comprising silver in an amount of about 2% by weight of the outer tubular later (3) and an inner tubular layer (4) of polyolefin having an inner tubular layer thickness (14) of about 0.381 millimeters which does not include an amount of antimicrobial agent (7).

Test Sample 4: a polymeric tubular conduit (1) including an outer tubular layer (3) of polyethylene terephthalate having an outer tubular layer thickness (13) thickness of about 0.127 millimeters which includes an amount of antimicrobial agent (7) comprising silver and zinc in a ratio of about 2:1 and in an amount of about 0.5% by weight of the outer tubular later (3) and an inner tubular layer (4) of polyolefin having an inner tubular layer thickness (14) of about 0.381 millimeters which does not include an amount of antimicrobial agent (7).

Test Sample 5: a polymeric tubular conduit (1) including an outer tubular layer (3) of polyethylene terephthalate having an outer tubular layer thickness (13) thickness of about 0.127 millimeters which includes an amount of antimicrobial agent (7) comprising silver and zinc in a ratio of about 2:1 and in an amount of about 1% by weight of the outer tubular later (3) and an inner tubular layer (4) of polyolefin having an inner tubular layer thickness (14) of about 0.381 millimeters which does not include an amount of antimicrobial agent (7).

Test Sample 6: a polymeric tubular conduit (1) including an outer tubular layer (3) of polyethylene terephthalate having an outer tubular layer thickness (13) thickness of about 0.127 millimeters which includes an amount of antimicrobial agent (7) comprising silver and zinc in a ratio of about 2:1 and in an amount of about 2% by weight of the outer tubular later (3) and an inner tubular layer (4) of polyolefin having an inner tubular layer thickness (14) of about 0.381 millimeters which does not include an amount of antimicrobial agent (7).

Test Method for *Escherichia coli* or *Staphylococcus aureus*

Basal Medium Eagle (BME) with Earle's salts and L-glutamine can be modified with calf/serum (10%) and 1.5% agar prior to being dispensed (15 mL) into Petri dishes. The agar-containing Petri dishes can be allowed to surface dry prior to inoculation with a lawn of *Escherichia coli* or *Staphylococcus aureus*. The inoculant can be prepared from Bactrol Discs available from Fisher Scientific which can be reconstituted as per the manufacturer's directions. Immediately after inoculation, one or more polymeric tubular conduits (1) can be placed on the surface of the agar. The Petri dishes can be incubated for about 24 hours at about 37° C. Following, the zone of inhibition can be measured and a corrected zone of inhibition can be calculated (corrected zone of inhibition equals zone of inhibition minus diameter of test material in contact with the agar).

Test Results

*Escherichia coli.*

The results can show no zone of inhibition associated with the control polymeric tubular conduit (1) and a zone of inhibition of about 0.5 millimeters around test samples 1 and 4, a zone of inhibition of about 5 millimeters around test samples 2 and 5, and a zone of inhibition of about 10 millimeters around test samples 3 and 6.

*Staphylococcus aureus.*

The results can show no zone of inhibition associated with the control polymeric tubular conduit (1) and a zone of inhibition of about 0.5 millimeters around test samples 1 and 4, a zone of inhibition of about 5 millimeters around test samples 2 and 5, and a zone of inhibition of about 10 millimeters around test samples 3 and 6.

Test Method for *Aspergillus niger, Cladosporium Cladosporioides*, or *Trichoderma* sp.

Sabouraud dextrose agar media (Biolife Vole Monza), pH 5.6, can be used for antifungal screening. Agar-containing Petri dishes can be allowed to surface dry prior to inoculation with a lawn of *Aspergillus niger, Cladosporium* cladosporioides, or *Trichoderma* sp. Immediately after inoculation, polymeric tubular conduits (1) can be placed on the surface of the agar. The Petri dishes can be incubated for about 72 hours at about 37° C. Following, the zone of inhibition can be measured and a corrected zone of inhibition can be calculated (corrected zone of inhibition equals zone of inhibition minus diameter of test material in contact with the agar).

Test Results

*Aspergillus niger.*

The results can show no zone of inhibition associated with the control polymeric tubular conduit (1) and a zone of inhibition of about 2 millimeters around test samples 1 and 4, a zone of inhibition of about 5 millimeters around test samples 2 and 5, and a zone of inhibition of about 13 millimeters around test samples 3 and 6.

*Cladosporium cladosporioides.*

The results can show no zone of inhibition associated with the control polymeric tubular conduit (1) and a zone of inhibition of about 4 millimeters around test samples 1 and 4, a zone of inhibition of about 8 millimeters around test samples 2 and 5, and a zone of inhibition of about 14 millimeters around test samples 3 and 6.

*Trichoderma* sp.

The results can show no zone of inhibition associated with the control polymeric tubular conduit (1) and a zone of inhibition of about 3 millimeters around test samples 1 and 4, a zone of inhibition of about 9 millimeters around test samples 2 and 5, and a zone of inhibition of about 15 millimeters around test samples 3 and 6.

A method of making a polymeric tubular conduit (1) can include providing a polymeric tubular conduit wall (2) having an outer tubular layer (3) coaxially overlaying an inner tubular layer (4) which defines a continuous tubular passage (5) along a polymeric tubular conduit length (6) of the polymeric tubular conduit (1), whereby the outer tubular layer (3) includes an amount of antimicrobial agent (7).

As to particular embodiments, the method can further include forming the inner tubular layer (4) from a first polymeric material (33) and forming the outer tubular layer (3) from a second polymeric material (34), whereby the amount of antimicrobial agent (7) can be combined with the second polymeric material (34) to provide the outer tubular layer (3) including an amount of antimicrobial agent (7).

Another method of making a polymeric tubular conduit (1) can include providing a polymeric tubular conduit wall (2) having an outer tubular layer (3) coaxially overlaying an inner tubular layer (4) which defines a continuous tubular passage (5) along a polymeric tubular conduit length (6) of the polymeric tubular conduit (1), whereby the inner tubular layer (4) includes an amount of antimicrobial agent (7).

As to particular embodiments, the method can further include forming the inner tubular layer (4) from a first polymeric material (33) and forming the outer tubular layer (3) from a second polymeric material (34), whereby the amount of antimicrobial agent (7) can be combined with the first polymeric material (33) to provide the inner tubular layer (4) including an amount of antimicrobial agent (7).

As to particular embodiments, the method can further include coextruding the first and second polymeric materials (33)(34) to form the polymeric tubular conduit (1) including the polymeric tubular conduit wall (2) having the outer tubular layer (3) coaxially overlaying the inner tubular layer (4).

As to particular embodiments, the method can further include cooling the coextruded polymeric tubular conduit (1) to a temperature below a softening point of the first and second polymeric materials (33)(34). As to particular embodiments, the cooled polymeric tubular conduit (1) can provide a drinking straw (17). As to other particular embodiments, the cooled polymeric tubular conduit (1) can provide medical tubing (26).

As to particular embodiments, the method can further include cutting the cooled polymeric tubular conduit (1) across the polymeric tubular conduit length (6) to provide a plurality of discrete polymeric tubular conduits (1). As to particular embodiments, the plurality of discrete polymeric tubular conduits (1) can provide a plurality of discrete drinking straws (17).

Now referring primarily to FIG. 6 through FIG. 8, the first and second polymeric materials (33)(34) (and, as to particular embodiments, additional polymeric materials (35) which can form one or more intermediate layers (16)) can be provided in the form of nurdles (36) which generally take the form of small granules or beads (also referred to as "resin"). Each of the first and second polymeric materials (33)(34) (and, as to particular embodiments, additional polymeric materials (36) which can form one or more intermediate layers (16)) can further include additives (37), such as plasticizers, fillers, pigments, colorants, ultraviolet radiation inhibitors, or the like, or combinations thereof, which can be included during production of the first and second polymeric materials (33)(34) (and, as to particular embodiments, additional polymeric materials (35) which can form one or more intermediate layers (16)) or can be provided as a liquid(s) or as a solid(s) which can be combined with the nurdles (36).

The antimicrobial agent (7) can be combined with the first or second polymeric materials (33)(34) (or, as to particular embodiments, additional polymeric materials (35) which can form one or more intermediate layers (16)) in the production of the nurdles (36) or combined as a discrete additive to the nurdles (36) to achieve a concentration of the antimicrobial agent (7).

Again referring primarily to FIG. 6 through FIG. 8, for coextrusion, the first and second polymeric materials (33)(34) (and, as to particular embodiments, additional polymeric materials (35) which can form one or more intermediate layers (16)), each in the form of nurdles (36), can each be disposed in a hopper (38) of corresponding first and second extruders (39)(40) (and, as to particular embodiments, additional extruders (41) which can receive the additional polymeric materials (35) which can form one or more intermediate layers (16)), whereby the nurdles (36) can be fed under influence of gravity through a feed throat (42) of the hopper (38) proximate a barrel rear end (43) of a barrel (44). A screw (45) rotatably journaled in the barrel (44) can contact the nurdles (36) entering the barrel rear end (43). A driver (46) operates to rotate the screw (45) inside the barrel (44), forcing the nurdles (36) toward a barrel front end (47) of the barrel (44). The rate at which the screw (45) rotates in the barrel (44) can be adjusted, but generally the screw (45) rotates up to about 120 revolutions per minute; however, the invention need not be so limited, as the screw (45) can rotate at any rate sufficient to move the nurdles (36) from the barrel rear end (43) toward the barrel front end (47), including rates lesser or greater than 120 revolutions per minute, depending upon the application. As to particular embodiments, the screw (45) can be driven at a continuous rate or at a variable rate, depending upon the application.

Now referring primarily to FIG. 6, as to each extruder (39)(40)(41), a heater (48) can be coupled to the barrel (44) to heat the barrel (44) to a desired temperature. One or more temperature sensors (49) can be disposed in relation to a barrel wall (50) to sense the temperature along the length of the barrel (44), which can be controlled to achieve the melt point of the nurdles (36) (the temperature at which the nurdles (36) begin to turn from a solid to a liquid, also referred to as "molten" polymeric material).

The melt point can vary greatly between different polymeric materials (33)(34)(35) but typically occurs within a range from between about 200° C. (392° F.) to about 275° C. (527° F.); however, particular polymeric materials (33)(34)(35) may have a melt point which occurs at a lesser or greater temperature. Further, the melt point can vary depending upon additives (37) introduced.

A heating profile can be set for the barrel (44) in which one or more temperature-controlled heater zones (51) gradually increase the temperature of the barrel (44) from the barrel rear end (43) to the barrel front end (47). This can allow the nurdles (36) of the first and second polymeric materials (33)(34) (and, as to particular embodiments, additional polymeric materials (35) which can form one or more intermediate layers (16)) to melt gradually as they are forced along the length of the barrel (44) toward the barrel front end (47).

The screw (45) acting on the nurdles (36) can generate an amount of pressure, friction, or combinations thereof, which can generate an additional amount of heat. The heat of the pressure, friction, or combinations thereof, can be sufficient to achieve or maintain the melt point of the first and second polymeric materials (33)(34) (and, as to particular embodiments, additional polymeric materials (35) which can form one or more intermediate layers (16)) inside the corresponding barrel (44). Each extruder (39)(40)(41) can further include a cooling element (52), such as a fan or water jacket, to maintain the temperature at or below a temperature set point.

Now referring primarily to FIG. 8, the molten first and second polymeric materials (33)(34) (and, as to particular embodiments, additional molten polymeric materials (35) which can form one or more intermediate layers (16)) can egress from the corresponding barrel (44) and can be forced through corresponding one or more screens (53) to remove any contaminants in the molten polymeric material (33)(34)(35). The one or more screens (53) can be reinforced by a breaker plate (54), which can take the form of a metal disk having a plurality bores communicating between opposed sides. The one or more screens (53) and breaker plate (54) acting on the corresponding molten polymeric material (33)(34)(35) can generate a substantial back pressure of the polymeric material (33)(34)(35) in the corresponding barrel (44). The configuration of the one or more screens (53) with respect to overall dimensional relations, wire size, total open area, or other parameters, and the configuration of the breaker plate (54) with respect to overall dimensional relations, bore size, total open area, or other parameters, can be adjusted to correspondingly adjust the amount of back pressure in the barrel (44) as required for uniform melting and proper mixing of the corresponding polymeric material (33)(34)(35). The back pressure can vary greatly depending upon the polymeric material (33)(34)(35), or additive, utilized, the configuration of the polymeric tubular conduit (1) being produced, or other parameters, typically occurring in a range of between about 1,000 psi (about 7 megapascals) to about 10,000 psi (about 70 megapascals); although particular applications may generate a lesser or greater back pressure. The breaker plate (54) can also function to convert "rotational memory" of the molten polymeric material (33)(34)(35) into "longitudinal memory" of the molten polymeric material (3)(34)(35).

Again referring primarily to FIG. 8, which provides an illustrative example of molten first and second polymeric materials (33)(34) passing through corresponding breaker plates (54) into a die (55) having a first die passage (56) which receives the first polymeric material (33) from the first extruder (39) and a second die passage (57) which receives the second polymeric material (34) from the second extruder (40). The first die passage (56) can be configured to generate the inner tubular layer (4) of the polymeric tubular conduit (1). The second die passage (57) can be configured to co-axially generate the outer tubular layer (3) about the inner tubular layer (4) of the polymeric tubular conduit (1) to provide the configurations of the polymeric tubular conduit (1) above described, including embodiments of the drinking straw (17) and the medical tubing (26).

Now referring primarily to FIG. 6 and FIG. 7, as the polymeric tubular conduit (1) (also referred to as an "extrudate"), including the inner tubular layer (4) formed from the first polymeric material (33) and the outer tubular layer (3) formed from the second polymeric material (34), egresses from the die (55), the extrudate can be cooled, for example by being drawn through a bath (58) containing an amount of coolant (59), which can typically, but not necessarily, be water. In the production of the polymeric tubular conduit (1) in accordance with the invention, the bath (58) can take the form of an elongate enclosure (60) having an extrudate inlet (61) mounted in relation to an inlet side (62) of the bath (58) and an extrudate outlet (63) mounted in relation to an outlet side (64) of the bath (58). The extrudate inlet (62) and the extrudate outlet (63) can correspondingly include an inlet seal (65) and an outlet seal (66) configured to sufficiently engage the polymeric tubular conduit wall external surface (8) to maintain a coolant level (67) within the bath (58) between the extrudate inlet (61) and the extrudate outlet (63) through which the polymeric tubular conduit (1) can be drawn for cooling. The remaining volume of the bath (58) can provide a headspace (68) within the bath (58).

Now referring primarily to FIG. 6, a vacuum generator (69) can operate to reduce pressure within the bath (58) in relation to the ambient pressure outside the bath (58), which can act at the inlet seal (65) and the outlet seal (66) to draw an amount of coolant (59) toward the bath interior volume, which can act on the still-molten polymeric tubular conduit (1) to counter a tendency toward collapse. Once cooled, the polymeric tubular conduit (1) can be wound on a spool (70), or cut into lengths for use as a drinking straw (17), medical tubing (26), or otherwise used or stored.

Now referring primarily to FIG. 1A and FIG. 1B, a method of using a polymeric tubular conduit (1) can include obtaining the polymeric tubular conduit (1) including a polymeric tubular conduit wall (2) having an outer tubular layer (3) coaxially overlaying an inner tubular layer (4) which defines a continuous tubular passage (5) along a polymeric tubular conduit length (6) of the polymeric tubular conduit (1), whereby the outer tubular layer (3) comprises an amount of antimicrobial agent (7); and drawing fluids through the continuous tubular passage (5). The amount of antimicrobial agent (7) can be sufficient to kill or inhibit growth of microorganisms which contact a polymeric tubular conduit wall external surface (8) of the polymeric tubular conduit wall (2). As to particular embodiments, the polymeric tubular conduit (1) can provide a drinking straw (17) (as shown in FIG. 1A). As to other particular embodiments, the polymeric tubular conduit (1) can provide medical tubing (26) (as shown in FIG. 1B).

As to other particular embodiments, a method of using a polymeric tubular conduit (1) can include obtaining the polymeric tubular conduit (1) including a polymeric tubular conduit wall (2) having an outer tubular layer (3) coaxially overlaying an inner tubular layer (4) which defines a continuous tubular passage (5) along a polymeric tubular conduit length (6) of the polymeric tubular conduit (1), whereby the inner tubular layer (4) comprises an amount of antimicrobial agent (7); and drawing fluids through the continuous tubular passage (5). The amount of antimicrobial agent (7) can be sufficient to kill or inhibit growth of microorganisms which contact a polymeric tubular conduit wall internal surface (9) of the polymeric tubular conduit wall (2). As to particular embodiments, the polymeric tubular conduit (1) can provide a drinking straw (17). As to other particular embodiments, the polymeric tubular conduit (1) can provide medical tubing (26).

As can be easily understood from the foregoing, the basic concepts of the present invention may be embodied in a variety of ways. The invention involves numerous and varied embodiments of an antimicrobial straw and methods for making and using such antimicrobial straws, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "inhibitor" should be understood to encompass disclosure of the act of "inhibiting"—whether explicitly discussed or not—and, conversely, were there effectively disclosure of the act of "inhibiting", such a disclosure should be understood to encompass disclosure of an "inhibitor" and even a "means for inhibiting". Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the antimicrobial straws herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A polymeric tubular conduit comprising:
a polymeric tubular conduit wall having an outer tubular layer coaxially overlaying an inner tubular layer which defines a continuous tubular passage along a polymeric tubular conduit length of said polymeric tubular conduit;
wherein said outer tubular layer comprises an amount of antimicrobial agent;
wherein said amount of antimicrobial agent is not greater than about 3% by weight of said outer tubular layer.

2. The polymeric tubular conduit of claim 1, wherein said amount of antimicrobial agent is sufficient to kill microorganisms which contact a polymeric tubular conduit wall external surface of said polymeric tubular conduit wall.

3. The polymeric tubular conduit of claim 1, wherein said amount of antimicrobial agent is sufficient to inhibit growth of microorganisms which contact a polymeric tubular conduit wall external surface of said polymeric tubular conduit wall.

4. The polymeric tubular conduit of claim 1, further comprising a polymeric tubular conduit wall thickness disposed between a polymeric tubular conduit wall external surface defined by an outer tubular layer external surface of said outer tubular layer and a polymeric tubular conduit wall internal surface defined by an inner tubular layer internal surface of said inner tubular layer, said polymeric tubular conduit wall thickness having a range of between about 0.05 millimeters to about 0.25 millimeters.

5. The polymeric tubular conduit of claim 4, wherein said polymeric tubular conduit wall thickness is selected from the group consisting of: between about 0.05 millimeters to about 0.1 millimeters; between about 0.075 millimeters to about 0.125 millimeters; between about 0.1 millimeters to about 0.15 millimeters; between about 0.125 millimeters to about 0.175 millimeters; between about 0.15 millimeters to about 0.2 millimeters; between about 0.175 millimeters to about 0.225 millimeters; and between about 0.2 millimeters to about 0.25 millimeters.

6. The polymeric tubular conduit of claim 1, wherein said amount of antimicrobial agent is in a range of between about 0.01% to about 3% by weight of said outer tubular layer.

7. The polymeric tubular conduit of claim 6, wherein said amount of antimicrobial agent is selected from the group consisting of: between about 0.01% to about 1% by weight of said outer tubular layer; between about 0.5% to about 1.5% by weight of said outer tubular layer; between about 1% to about 2% by weight of said outer tubular layer; between about 1.5% to about 2.5% by weight of said outer tubular layer; and between about 2% to about 3% by weight of said outer tubular layer.

8. The polymeric tubular conduit of claim 6, wherein said antimicrobial agent comprises an amount of one or more selected from the group consisting of: silver and zinc.

9. The polymeric tubular conduit of claim 8, wherein said amount of silver is less than about 2% by weight of said outer tubular layer.

10. The polymeric tubular conduit of claim 9, wherein said polymeric tubular conduit forms a drinking straw comprising:
a drinking straw wall having a drinking straw outer tubular layer coaxially overlaying a drinking straw inner tubular layer which defines a drinking straw continuous tubular passage along a drinking straw length of said drinking straw;
wherein said drinking straw outer tubular layer comprises an amount of antimicrobial agent.

11. The polymeric tubular conduit of claim 10, wherein said amount of antimicrobial agent is sufficient to kill microorganisms which contact a drinking straw wall external surface of said drinking straw wall.

12. The polymeric tubular conduit of claim 10, wherein said amount of antimicrobial agent is sufficient to inhibit growth of microorganisms which contact a drinking straw wall external surface of said drinking straw wall.

13. The polymeric tubular conduit of claim 9, wherein said polymeric tubular conduit forms medical tubing comprising:
a medical tubing wall having a medical tubing outer tubular layer coaxially overlaying a medical tubing inner tubular layer which defines a medical tubing continuous tubular passage along a medical tubing length of said medical tubing;
wherein said medical tubing outer tubular layer comprises an amount of antimicrobial agent.

14. The polymeric tubular conduit of claim 13, wherein said amount of antimicrobial agent is sufficient to kill microorganisms which contact a medical tubing wall external surface of said medical tubing wall.

15. The polymeric tubular conduit of claim 13, wherein said amount of antimicrobial agent is sufficient to inhibit growth of microorganisms which contact a medical tubing wall external surface of said medical tubing wall.

16. The polymeric tubular conduit of claim 1, furthering comprising at least one intermediate layer disposed between said inner and outer tubular layers.

17. A polymeric tubular conduit comprising:
a polymeric tubular conduit wall having an outer tubular layer coaxially overlaying an inner tubular layer which defines a continuous tubular passage along a polymeric tubular conduit length of said polymeric tubular conduit;
wherein said outer tubular layer comprises an amount of antimicrobial agent; and
wherein said antimicrobial agent has a median particle size distribution which is not less than about 0.5 micrometers.

18. The polymeric tubular conduit of claim 17, wherein said median particle size distribution is in a range of between about 0.5 micrometers to about 15 micrometers.

19. A polymeric tubular conduit comprising:
a polymeric tubular conduit wall having an outer tubular layer coaxially overlaying an inner tubular layer which defines a continuous tubular passage along a polymeric tubular conduit length of said polymeric tubular conduit;
wherein said outer tubular layer comprises an amount of antimicrobial agent; and
wherein said antimicrobial agent comprises silver-containing zeolites, wherein an amount of silver ions in said silver-containing zeolites is in the range of between 0.5% to about 20% by weight of said silver-containing zeolites.

* * * * *